United States Patent
Nielsen et al.

(10) Patent No.: US 7,516,662 B2
(45) Date of Patent: Apr. 14, 2009

(54) DETECTING RAIL DEFECTS

(75) Inventors: Steen Arnfred Nielsen, Jyllinge (DK); Alexander Bardenshtein, Hedehusene (DK); Niels Kloppenborg Laursen, Rosklide (DK)

(73) Assignees: Force Technology, Brondby (DK); Banestyrelsen, Copenhagen O (DK)

( * ) Notice: Subject to any disclaimer, the term of this patent is extended or adjusted under 35 U.S.C. 154(b) by 304 days.

(21) Appl. No.: 10/587,289

(22) PCT Filed: Jan. 25, 2005

(86) PCT No.: PCT/DK2005/000050
§ 371 (c)(1), (2), (4) Date: Jul. 25, 2006

(87) PCT Pub. No.: WO2005/070743
PCT Pub. Date: Aug. 4, 2005

(65) Prior Publication Data
US 2007/0163352 A1    Jul. 19, 2007

(30) Foreign Application Priority Data
Jan. 26, 2004    (DK) .............................. 2004 00100

(51) Int. Cl.
G01N 29/04    (2006.01)
(52) U.S. Cl. .......................................... 73/598; 73/636
(58) Field of Classification Search ........... 73/655–657, 73/625–626, 602, 502–503, 596–600; 356/345, 356/349, 357–360, 432
See application file for complete search history.

(56) References Cited

U.S. PATENT DOCUMENTS

| 4,712,722 | A | 12/1987 | Hood et al. |
| 5,574,224 | A | 11/1996 | Jaeggi |
| 6,382,028 | B1 * | 5/2002 | Wooh et al. ................... 73/602 |
| 7,278,305 | B2 * | 10/2007 | Kilian et al. .................. 73/146 |
| 7,278,315 | B1 * | 10/2007 | Klein et al. ................... 73/602 |
| 2001/0020390 | A1 | 9/2001 | Wooh |
| 2004/0003662 | A1 | 1/2004 | Kenderian et al. |

FOREIGN PATENT DOCUMENTS

| EP | 1 236 634 A1 | 9/2002 |
| GB | 2388413 A | 6/2003 |

OTHER PUBLICATIONS

Shi-Chang Wooh et al., "Laser Ultrasonic Detection of Rail Defects", Review of Quantitative Nondestructive Evaluation, vol. 21, p. 1819-1826, 2002.

* cited by examiner

Primary Examiner—Helen C. Kwok
(74) Attorney, Agent, or Firm—Day Pitney LLP

(57) ABSTRACT

A method of detecting defects in a railway track rail, the rail (101) having a longitudinal centre plane and a surface, the surface including a running surface (102), the method comprising directing an excitation laser beam (106) to an excitation position (103) on the surface of the rail (101) to induce an ultrasonic wave in the rail (101); and directing a detection laser beam (108) to a detection position (104) on the surface of the rail (101) to detect at least one predetermined property of the induced ultrasonic wave; wherein the excitation position (103) and the detection position (104) are located on the running surface (102) and displaced from the longitudinal centre plane of the rail (101).

26 Claims, 6 Drawing Sheets

DETECTING RAIL DEFECTS

BACKGROUND OF THE INVENTION

The present invention relates to the detection of defects in railway track rails.

Railway track rails can develop a number of different defects/flaws/faults during manufacturing and/or during the operational life time of the rails. There are a number of different types of defects, and the International Union of Railways (UIC) has defined a standard system for classifying broken, cracked and damaged rails.

UK patent application GB 2 383 413 describes a system for detecting rail defects using acoustic surface waves. This prior art system comprises an ultrasonic transmit transducer and a plurality of receive transducers positioned along the rail at different distances from the transducer. A degree of probability that there is a fault at a rail location is computed from measured changes in the spectral components of a surface wave.

It is a disadvantage of the above prior art technique that it requires contact of the transducers with the rail.

The article "Laser ultrasonic detection of rail defects" by Shi-Chang Wooh et al., in Review of Quantitative Nondestructive Evaluation, Vol. 21, ed. By D. O. Thompson et al., pp. 1819-1826, American Institute of Physics, 2002, discloses a method of characterising rail defects using a laser ultrasonic scanning technique and by analysing shadow patterns produced by shear waves. Even though this method provides a non-contact detection and characterisation of transverse defects in the rail head, this prior art method is limited to the detection of a certain defect type.

SUMMARY OF THE INVENTION

According to a first aspect it is an object of the invention to provide a non-contact method of detecting rail defects that can detect a plurality of different defect types.

It is a further object of the invention to provide a reliable detection of the defect type and the approximate location of the defect within the rail.

The above and other objects are achieved by a method of detecting defects in a railway track rail, the rail having a longitudinal centre plane and a surface, the surface including a running surface, the method comprising directing an excitation laser beam to an excitation position on the surface of the rail to induce an ultrasonic wave in the rail; and directing a detection laser beam to a detection position on the surface of the rail to detect at least one predetermined property of the induced ultrasonic wave;

wherein the excitation position and the detection position are located on the running surface and displaced from the longitudinal centre plane of the rail.

It has been realised by the inventors that a plurality of defect types can reliably be detected when the excitation position and the detection position are located on the running surface and displaced with respect to the longitudinal centre plane of the rail.

In particular, the following types of structural defects have been successfully detected by the method according to the invention:

1) horizontal cracking at the fillet radius between the web and the head of the rail (UIC code 2321)
2) longitudinal vertical cracks in the rail head (UIC Code 213)
3) horizontal cracking of the rail head (UIC Code 212)
4) progressive transverse cracking of the rail head (UIC Code 211)
5) long groove at the running surface (UIC Code 221.2), and
6) complete rail break.

It is understood, however, that the invention may also be applied in the detection of other types of structural defects in rails.

It has turned out that a particularly reliable detection of in particular the first, third, fourth and sixth of the above types of defects is achieved when the excitation position is located on a first side of the longitudinal centre plane and when the detection position is located on a second side of the longitudinal centre plane opposite the first side, thereby providing a particularly high interaction cross section of the ultrasonic wave with the rail defects. The detection of the above defect types is further improved when the excitation position is displaced from the longitudinal centre plane by an excitation distance; and when the detection position is displaced from the longitudinal centre plane by a detection distance, the detection distance being substantially equal to the excitation distance, i.e. when the detection position and the excitation position are located substantially equidistant around the longitudinal centre plane of the rail.

It is further preferred that the rail comprises a rail web portion supporting a rail head, the rail web portion having a web waist defining a minimum cross sectional width of the rail web; and that the detection position is displaced from the excitation position in a cross direction of the rail by a transverse spot displacement corresponding to half the minimum cross sectional width of the rail web.

In a particularly preferred embodiment, the detection position is displaced in the longitudinal direction of the rail from the excitation position by a longitudinal spot displacement. Most preferably the rail comprises a rail head having a predetermined width, and the longitudinal spot displacement corresponds to a half the width of the rail head, thereby obtaining a particularly reliable detection of the defects.

It has further turned out that a particularly reliable detection of in particular the second and fifth of the above types of defects is achieved when the rail comprises a gage side proximate to a centre of the railway track; and when the excitation position and the detection position are located on the gage side of the longitudinal axis.

In a particularly preferred embodiment, the rail comprises a rail web portion supporting a rail head, the rail web portion having a web waist defining a minimum cross sectional width of the rail web; and the detection position is displaced from the longitudinal centre plane by a detection distance corresponding to half the minimum cross sectional width of the rail.

According to yet another preferred embodiment, the excitation spot is an elongated spot, preferably having a longitudinal dimension of several millimeters, such as between 1 and 10 mm. It is an advantage of an elongated or linear excitation laser-beam spot that it results in ultrasonic waves which experience a significantly lower geometrical attenuation when propagating through the rail. Furthermore, elongated or linear beam spots provide an improved suppression of undesired background waves arriving at the detection spot. Consequently, an elongated excitation spot results in an improved signal-to-noise ratio. The length of the elongated spot may be adjusted to optimise the signal-to-noise ratio by balancing the attenuation of the generated waves with the generated power density. Larger longitudinal spot sizes, i.e. long elongated spots, provide a lower attenuation while shorter spot sizes increase the power density and, thus, the amplitude of the generated ultrasound wave. Spot sizes of 3-5 mm have been found to be particularly advantageous in the context of detecting rail defects.

Preferably, the elongated spot defines a longitudinal excitation spot direction, and the longitudinal excitation spot direction is transverse with respect to the direction of the displacement of the detection position from the excitation position.

It is desirable to provide a detection technique that allows an efficient testing of a large railway network. Accordingly, it is preferred that the detection position and the excitation position are moved along the longitudinal direction of the rail at a predetermined speed.

It is an advantage of the present invention that it provides a detection method that is well-suited for reliably detecting defects in a rail, even when the detector is moved along the rail.

In particular, since the laser beams are directed to the running surface of the rail, i.e. directed to the rail from above the rail, the lasers may be moved along the rail without the risk of being damaged, e.g. when passing points, crossing, or the like.

It is a further advantage that the method provides a non-contact measurement, i.e. measurements that do not require physical contact between the detector and the rail, thereby allowing for a movement of the detector along the rail during the measurement at relatively high speed.

In yet another preferred embodiment, the method further comprises obtaining a first ultrasonic waveform corresponding to an ultrasonic wave induced into a first rail segment;

dividing the first ultrasonic waveform into a set of waveform segments;

determining at least a first waveform parameter indicative of at least one predetermined property of a first waveform segment;

determining the first waveform segment as being indicative of the presence or absence of a rail defect in the first rail segment by comparing the determined first waveform parameter with at least one reference waveform parameter.

It is an advantage of the invention that it utilises information from different segments of the acquired waveform, thereby utilising information from different types of ultrasonic waves propagating at different speeds and in different directions, and allowing the detection of different types of defects. According to the invention, a plurality of waveforms, e.g. longitudinal waves, shear waves, and Rayleigh waves, are detected and used to detect and characterise rail defects.

Further preferred embodiments are disclosed in the dependent claims.

The present invention can be implemented in different ways including the method described above and in the following and an apparatus, each yielding one or more of the benefits and advantages described in connection with the first-mentioned method, and each having one or more preferred embodiments corresponding to the preferred embodiments described in connection with the first-mentioned method.

In particular, the invention further relates to an apparatus for detecting defects in a railway track rail, the rail having a longitudinal centre plane and a surface, the surface including a running surface, the apparatus comprising an excitation laser arrangement adapted to direct an excitation laser beam to an excitation position on the surface of the rail to induce an ultrasonic wave in the rail; and a detection laser arrangement adapted to direct a detection laser beam to a detection position on the surface of the rail to detect a predetermined property of the induced ultrasonic wave;

The excitation laser arrangement and the detection laser arrangement are arranged to direct the excitation laser beam and the detection laser beam to respective excitation and detection positions located on the running surface and displaced from the longitudinal centre plane of the rail.

In a preferred embodiment, the apparatus further comprises a rail vehicle adapted to be moved along the rail; wherein the excitation laser arrangement and the detection laser arrangement are mounted to the rail vehicle. Hence, the apparatus may be moved along the rail allowing the testing of a large network of railway tracks.

In another preferred embodiment, the apparatus further comprises control means for adjusting the incident angle of the detection laser beam on the running surface of the rail, thereby providing a detection laser beam having a substantially constant incident angle, or at least an incident angle within a predetermined interval, even if the running surface is inclined. Preferably, the apparatus further comprises means for detecting an incident angle, in particular an incident angle deviating from a desired incident angle by more than a predetermined tolerance.

According to a second aspect it is an object of the present invention to provide a reliable method of detecting defects in a railway track rail that provides a reliable detection of different defect types.

The above and other objects are achieved by a method of detecting defects in a railway track rail, the method comprising obtaining a first ultrasonic waveform corresponding to an ultrasonic wave induced into a first rail segment;

dividing the first ultrasonic waveform into a set of waveform segments;

determining at least a first waveform parameter indicative of at least one predetermined property of a first waveform segment;

determining the first waveform segment as being indicative of the presence or absence of a rail defect in the first rail segment by comparing the determined first waveform parameter with at least one reference waveform parameter.

It is an advantage of the invention that it utilises information from different segments of the acquired waveform, thereby utilising information from different types of ultrasonic waves propagating at different speeds and in different directions, thereby allowing the detection of different types of defects.

In a preferred embodiment, the at least one predetermined property includes at least one of a standard deviation and a peak height. Hence, the detection is based on parameters that can efficiently and reliably be detected from the waveform, in particular from an A-scan representing amplitude as a function of time.

It is a further advantage of the invention that it analyses the acquired ultrasonic A-scans directly, thereby avoiding complex additional processing such as Fourier Transformations, or the like.

In a further preferred embodiment, the at least one reference waveform parameter includes at least one of a waveform parameter of a corresponding waveform segment of a calibration waveform and a waveform parameter of a second waveform segment of the first ultrasonic waveform, the second waveform segment being adjacent to the first waveform segment. It is a further advantage of the invention that it performs an automatic detection of defects by comparing the A-scan segments with corresponding reference or calibration A-scans of rail sections without defects, thereby providing a reliable automatic detection. It is a further advantage that the detection only relies on little a priori information about the rail, thereby further increasing the reliability and flexibility of the method.

By further comparing the waveform property of a segment/window of the waveform with the corresponding properties of adjacent segments/windows, the detection reliability is further improved.

Further preferred embodiments are disclosed in the dependent claims.

It is noted that the features of the method described above and in the following may be implemented in software and carried out on a data processing system or other processing means caused by the execution of program code means such as computer-executable instructions. Here and in the following, the term processing means comprises any circuit and/or device suitably adapted to perform the above functions. In particular, the above term comprises general- or special-purpose programmable microprocessors, Digital Signal Processors (DSP), Application Specific Integrated Circuits (ASIC), Programmable Logic Arrays (PLA), Field Programmable Gate Arrays (FPGA), special purpose electronic circuits, etc., or a combination thereof.

For example, the program code means may be loaded in a memory, such as a RAM, from a storage medium or from another computer via a computer network. Alternatively, the described features may be implemented by hardwired circuitry instead of software or in combination with software.

In one embodiment, the data processing system comprises circuitry or a device for receiving waveform data, e.g. a data acquisition board, a parallel or serial interface, a network interface, a device for reading waveform data from a data carrier, e.g. from a CD ROM or the like.

BRIEF DESCRIPTION OF THE DRAWINGS

The above and other aspects of the invention will be apparent and elucidated from the embodiments described in the following with reference to the drawing in which.

DETAILED DESCRIPTION OF THE PREFERRED EMBODIMENT

Figure 1:
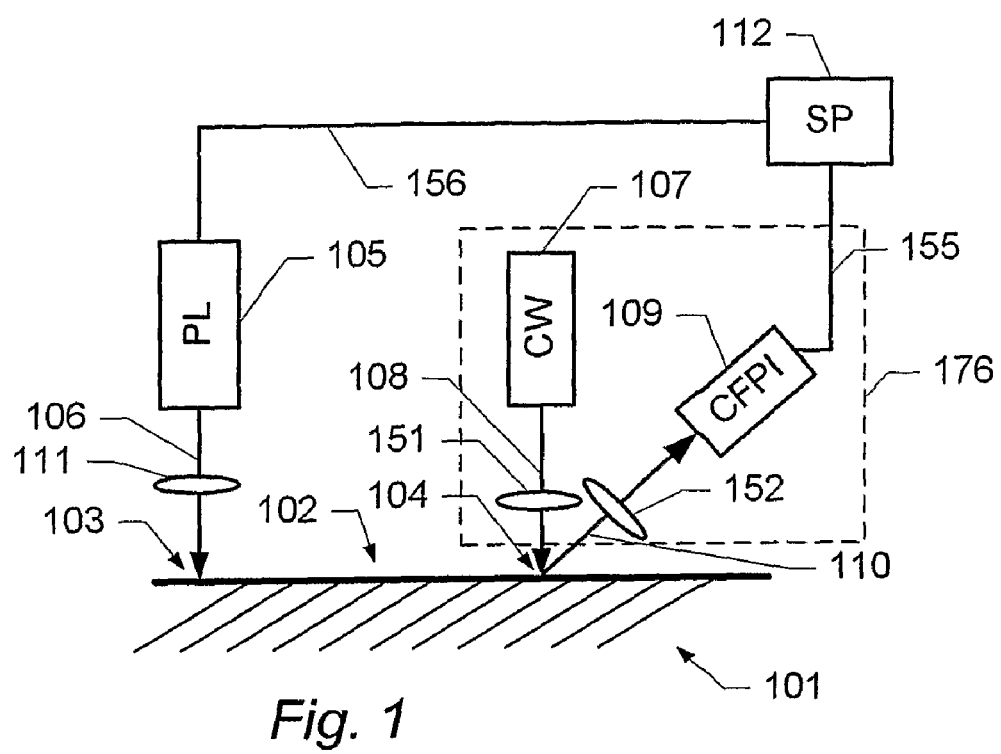
FIG. 1 shows a schematic block diagram of a device for detecting defects in rails.

FIG. 1 shows a schematic block diagram of a device for detecting defects in rails. The device comprises a laser beam source 105 which directs an excitation laser beam 106 to an excitation position 103 on the running surface 102 of a rail 101. In one embodiment, the laser beam source includes a pulsed, high repetition frequency laser, e.g. with a repetition frequency of 500 Hz or more. In one embodiment a pulse duration of 10 ns (FWHM) was used with a peak power of the laser of 2-3 MW. In one embodiment, a pulsed Nd:YAG laser is used. The laser beam 106 is focussed by a cylindrical lens 111 or other suitable optical arrangement on the rail surface 102 as an elongated focal spot. The power density of the laser is selected sufficiently high to ablate the rail surface, i.e. the laser-ultrasonic generation is operated in the ablation or plasma regime. The pulsed laser beam 106 generates ultrasound pulses in the rail originating from the excitation position 103, i.e. the excitation position 103 may be regarded as an ultrasonic source. The elongated or linear laser-beam spot results in planar laser-generated ultrasonic surfaces waves and cylindrical bulk waves.

Planar waves do not experience any geometrical attenuation with the flight distance r, while the geometrical attenuation of cylindrical waves is proportional to $r^{-1/2}$. In comparison a point-like (i.e. circular) spot excites circular surface waves and spherical bulk waves with a geometrical attenuation proportional to $r^{-1/2}$ and $r^{-1}$, respectively. Hence, the geometrical attenuation is significantly lower in the case of a linear source for both the surface and the bulk waves. Long spot sizes increase the degree of planarity/cylindricality of the waves.

The arrangement further comprises a detection device 176 comprising a continuous wave (CW) detection laser source 107 that directs a detection laser beam 108 to a detection position 104 on the running surface 102 of the rail 101. In one embodiment, the laser operates in the visible or near-infrared range. A CW detection laser provides a high data acquisition rate, thereby allowing an inspection of rails even at high speeds. In one embodiment, a CW diode-pumped Nd:YAG laser with a wavelength of 532 nm and an intensity of 200 mW was used. The detection laser beam 108 is focused by a spherical lens 151 or another suitable optical arrangement into a point-like focal spot 104.

Preferred embodiments of the positions of the focal spots 203 and 204 will be described in connection with FIGS. 2a-b and 3a-c, respectively.

The detection laser beam 108 is scattered/reflected on the surface 102 resulting in a scattered/reflected detection laser beam 110. The scattered/reflected detection laser beam is modulated by the motion of the reflecting surface via a Doppler shift of the frequency of the scattered/reflected detection laser beam.

The frequency shift of the scattered/reflected detection laser beam 110 is detected by a confocal Fabry-Perot interferometer (CFPI) 109. To this end, the scattered/reflected detection laser beam 110 is collected by lens 152 or by another suitable optical arrangement and directed into the CFPI 109.

The CFPI is arranged to have a resonance frequency corresponding to the frequency f of the detection laser. Preferably, the resonance frequency of the CFPI is controlled to be slightly displaced with respect to the frequency f of the detection laser beam, such that the laser frequency f is located on the slope (generally at half maximum height) of the resonance peak of the Fabry-Perot cavity. For example, the Fabry-Perot interferometer may be constructed and controlled as described in U.S. Pat. No. 5,080,491 which describes Fabry-Perot interferometers for use in ultrasound detection systems operated in reflection mode, in transmission mode, or in twin mode. The CFPI detects the frequency shift of the scattered/reflected detection laser beam 110 with respect to the resonance frequency of CFPI cavity. The CFPI generates a detection signal 155 representing measured light intensity as a function of time. The detection signal is indicative of the modulation of the scattered/reflected detection laser beam 110 caused by the motion of the surface 102 which, in turn, is caused by the ultrasonic wave induced by the excitation laser beam 106 and propagated through or along the surface of the rail. Since the ultrasonic wave interacts with defects in the rail, the detection signal carries information about such defects.

Figure 6:
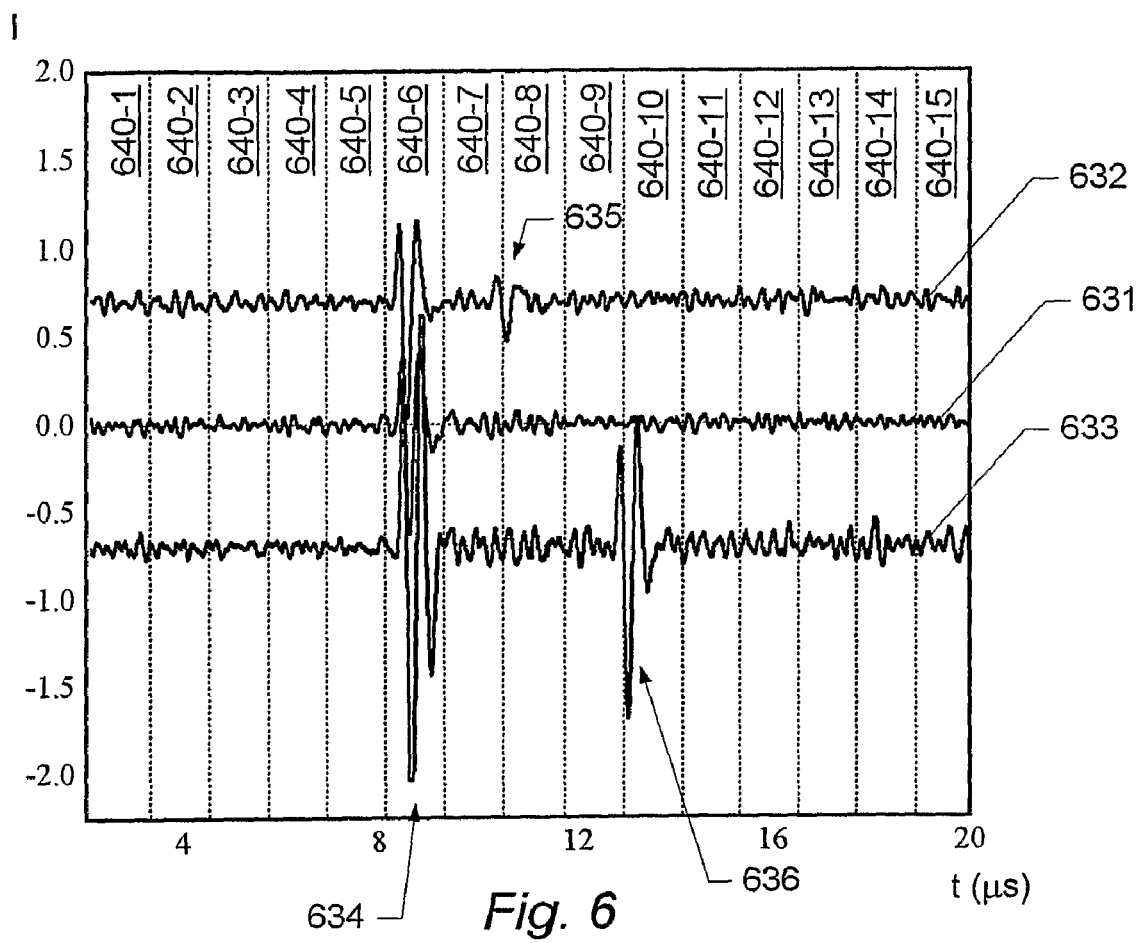
FIG. 6 illustrates examples of ultrasound waveforms of rails.
Figure 6A:
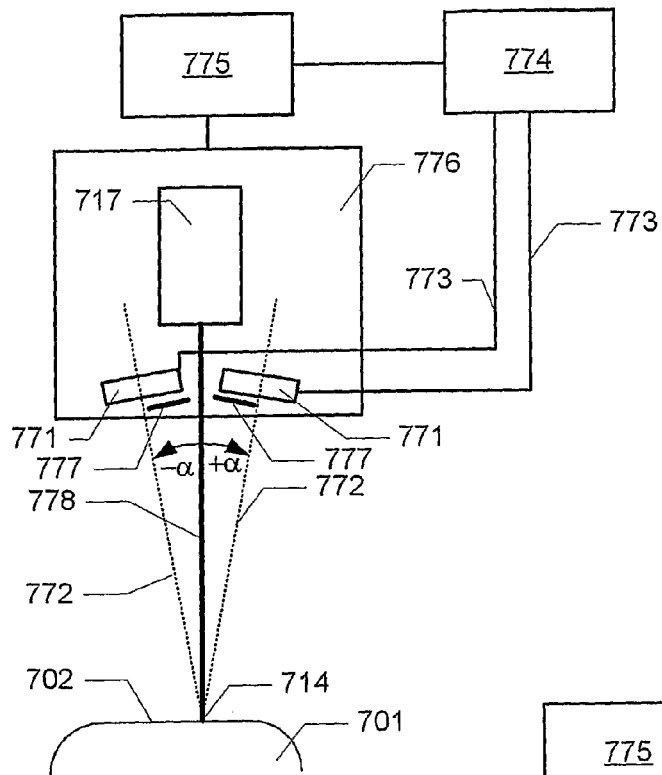

The detection signal 155 is fed into a signal processing unit 112, e.g. a computer or microprocessor comprising a data acquisition circuit providing a sampling rate sufficiently high to keep pace with the repetition rate of the generating pulsed laser. FIG. 6 below shows examples of detection signals, so-called A-scans, representing the detected light intensity and, thus, the intensity of the surface motion as a function of time. The signal processing unit 112 further receives a trigger signal 156 from the excitation laser source 105 indicative of the times at which the excitation laser source 105 fires a laser pulse to the surface 102.

The signal processing unit 112 processes the received detection signal and provides estimates of the type and location of any detected defects in the rail. An embodiment of the processing of the detection signal will be described in greater detail below.

Hence, in the above, a non-contact detection method is disclosed. It is an advantage of laser-ultrasound detection that it provides a high spatial resolution of the detection, due to the high bandwidth of the laser-generated pulses. Consequently a highly reliable defect detection is provided. It is a further advantage, that no physical contact of the detector with the rail is required.

It is an advantage of the CFPI detector that it provides fast reaction times, thereby allowing defect detection of a rail while the detector moves along the rail, even at speeds of 40-50 km/h or even higher speeds.

It is understood that, in alternative embodiments, other ultrasound detectors may be used, e.g. a photo electromotive force (photo-emf) detector.

Figure 2A:
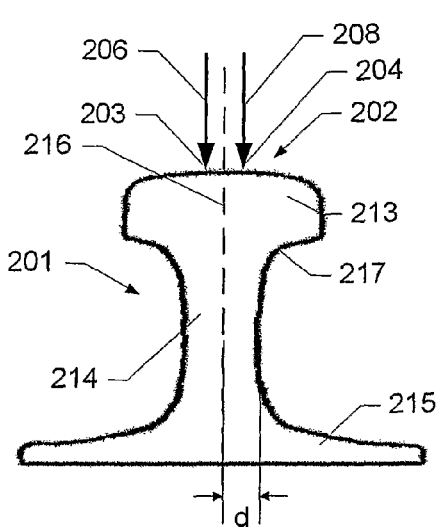
FIGS. 2a-b illustrate the positions of the excitation and detection laser beams on the rail according to a first embodiment of the invention.
Figure 2B:
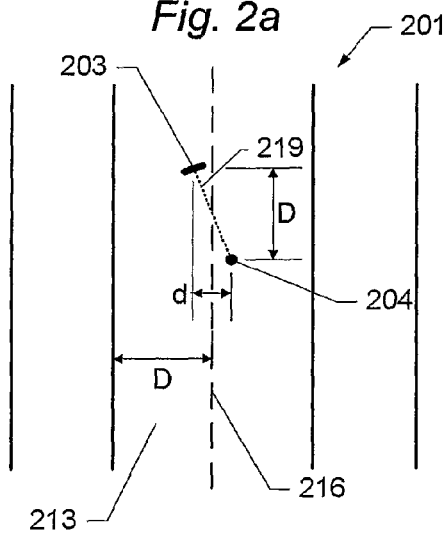

FIGS. 2a-b illustrate the positions of the excitation and detection laser beams on the rail according to a first embodiment of the invention. FIG. 2a shows a cross sectional view of a rail 201 and FIG. 2b shows a top view of the rail 201. The rail comprises a head portion 213 that provides a running surface 202 for railway wheels. The head portion 213 is supported by rail web 214 that extends downwards from the head 213 and towards a foot portion 215. The rail defines a longitudinal centre plane 216, and the rail web defines a minimal width of the rail, corresponding to a minimal half-width d measured from the longitudinal centre plane to the waist of the rail web 214. The rail head has a half-width D measured from the longitudinal centre plane 216 of the rail. The actual dimensions of the rail may vary. For example, the UIC 60 standard rail section has a minimum web thickness of 16.5 mm, i.e. d=8.25 mm and a head width of 72 mm, i.e. D=36 mm.

As mentioned above, there are different types of rail defects that can be detected and characterised according to the invention, including the following types of structural defects (the corresponding UIC codes are referred to in parenthesis):

1) horizontal cracking at the fillet radius 217 between the web 214 and the head 213 of the rail 201 (UIC code 2321)
2) longitudinal vertical cracks in the rail head 213 (UIC Code 213)
3) horizontal cracking of the rail head 213 (UIC Code 212)
4) progressive transverse cracking of the rail head 213 (UIC Code 211)
5) long groove at the running surface 212 (UIC Code 221.2), and
6) complete rail break.

The excitation laser beam 206 is directed to an excitation position 203 on the running surface 202 of the rail, and the detection laser beam 208 is directed to a detection position 204 on the running surface 202 of the rail. In a preferred embodiment, the excitation position 203 and the detection position are located on respective sides of the longitudinal centre plane 216, i.e. they are displaced from the centre plane and located on opposite sides of the centre plane. Preferably, the transverse spot displacement of the excitation position from the detection position, i.e. the displacement in transverse direction, corresponds to the half-width d of the waist of the rail web. It has been found that tolerances of the spot displacement and the displacement from the centre line as large as the length of the elongated spot size are acceptable. Furthermore, it is preferred that the detection position 204 is displaced from the excitation position in the longitudinal direction of the rail. The preferred longitudinal displacement corresponds to the half-width D of the rail head, e.g. lies in the interval 0.5·D-2·D, preferably 0.9·D-1.5·D. It is been found that, in a particularly preferred embodiment, the longitudinal displacement is selected from the interval 0.94·D-1.1·D, since this interval provides a required directivity of the shear wave at angle 40-45° in the rail head. Furthermore, it has been found that it is preferred to position the excitation spot on the gage side of the rail. This asymmetry is related to the fact that the probability of defect initiation on the gage side is higher than on the opposite side. In the longitudinal direction, the detection spot may be positioned before or after the excitation position with respect to the direction of the movement of the detection device along the rail.

Preferably, the laser beams are incident substantially perpendicular to the upper surface of the rail.

The excitation beam 206 is linearly focused resulting in an elongated focal spot 203. Preferably, the elongated focal spot 203 is oriented such that the detection position 204 is located on a perpendicular line 219 dropped from the centre of the elongated spot 203 perpendicular to the longitudinal direction of the elongated spot 203.

The above location of the excitation and detection positions has proven to be particularly advantageous for the detection of the first, third, fourth, and sixth of the above defect types, since these locations provide a high ultrasound interaction cross-section with these types of defects.

Figure 3A:
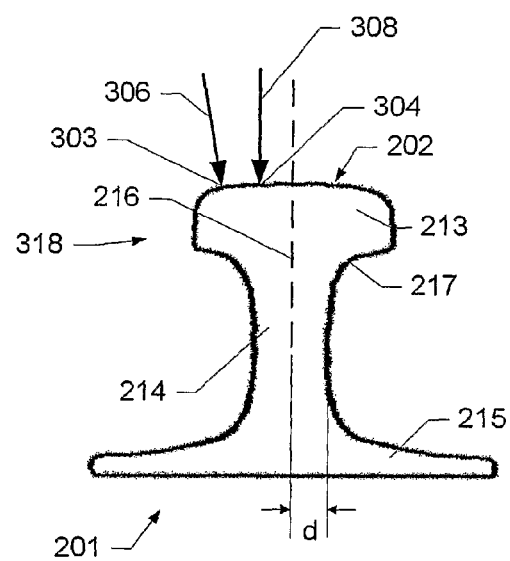
FIGS. 3a-c illustrate the positions of the excitation and detection laser beams on the rail according to a second embodiment of the invention.
Figure 3B:
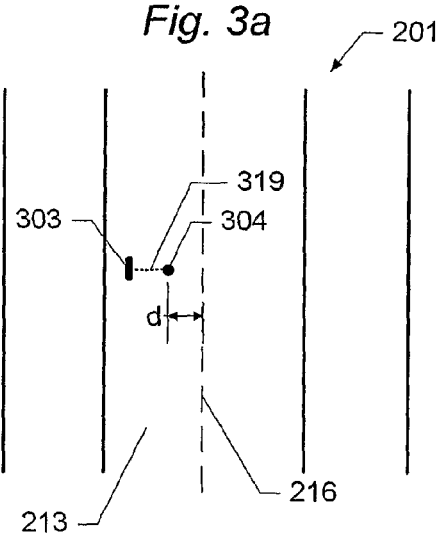
Figure 3C:
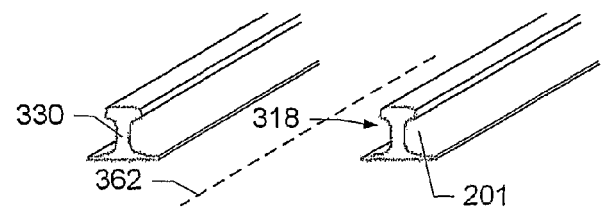

FIGS. 3a-c illustrate the positions of the excitation and detection laser beams on the rail according to a second embodiment of the invention. FIGS. 3a and 3b show a cross sectional view and a top view, respectively, of the rail 201 of FIGS. 2a-b, where like reference numerals refer to like elements already described in connection with FIGS. 2a-b. FIG. 3c shows a perspective view of the rail 201 when placed as part of a railway track including two rails 201 and 330. The side 318 of the rail 201 facing the other rail 330 of the railway track is referred to as the gage side of the rail. Hence, the gage side 318 is the side of the rail proximate to the centre line 362 of the railway track.

According to this embodiment, the excitation laser beam 306 is directed to an excitation position 303 on the running surface 202 of the rail, and the detection laser beam 308 is directed to a detection position 304 on the running surface 202 of the rail, such that the excitation position 303 and the detection position 304 are located on the gage side 318 of the longitudinal centre plane 216. Preferably, the detection spot is located proximate to the centre plane and the excitation spot is located distal to the centre plane, i.e. proximate to the edge of the running surface. It is preferred that the transverse displacement of the detection spot 304 from the longitudinal centre plane 216 corresponds to the half-width d of the waist of the rail web. It has been found that tolerances of the transverse displacement as large as the length of the elongated spot size are acceptable.

As in the previous embodiment, the excitation beam 306 is linearly focussed resulting in an elongated focal spot 303. Preferably, the elongated focal spot 303 is oriented along the longitudinal direction of the rail, i.e. substantially parallel to the centre plane 216. Furthermore, the detection position 204 is located on a perpendicular line 319 dropped from the centre of the elongated spot 303 perpendicular to the longitudinal direction of the elongated spot 203.

The above location of the excitation and detection positions has proven to be particularly advantageous for the detection of the second and fifth of the above defect types, since these locations provide a high ultrasound interaction cross-section with these types of defects.

Figure 4:
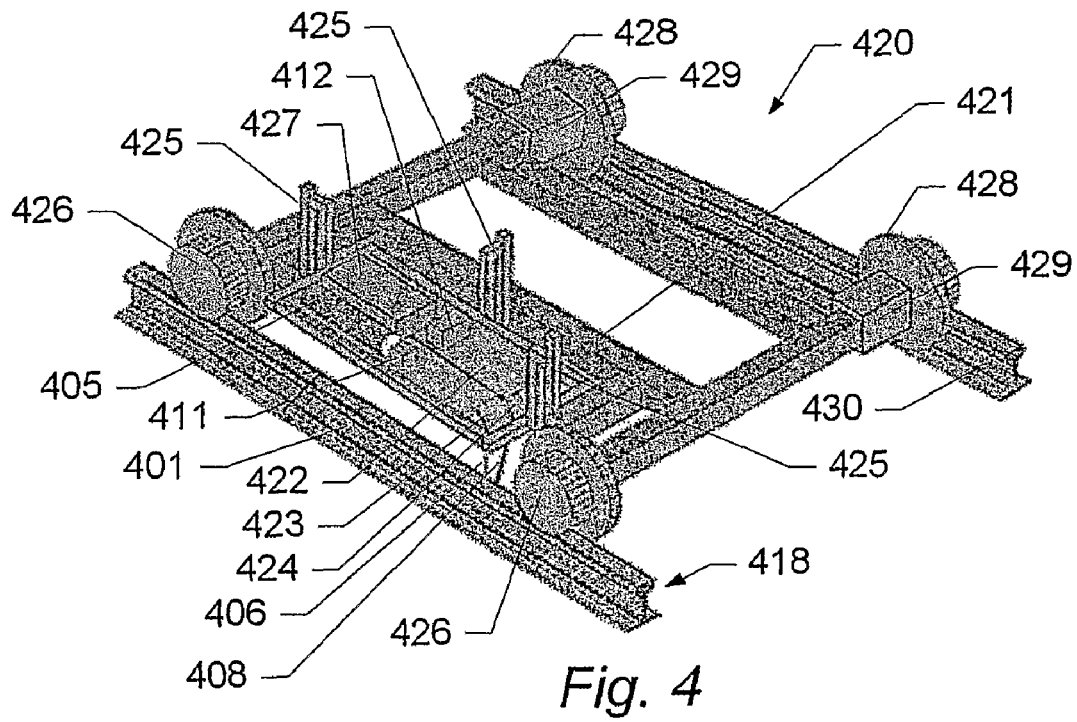
FIG. 4 schematically shows a rail vehicle having mounted thereon an arrangement for detecting defects in rails.

FIG. 4 schematically shows a rail vehicle having mounted thereon an arrangement for detecting defects in rails. The rail vehicle, generally designated 420, comprises a metal frame structure 421 and railway wheels 426 and 428 supporting the frame structure when the vehicle is moved along the rails 401 and 430 of a railway track. The rail vehicle 420 carries an arrangement for detecting defects in one of the rails of a railway track along which the vehicle is moved, e.g. by suspending the vehicle under a maintenance railway vehicle. A platform 422 is connected to the frame structure 421. An excitation laser 405 is mounted on the platform 422 together with a corresponding optical system 411 for focussing the excitation laser beam 406 on the running surface of the rail 401 via a mirror 423. Furthermore, an ultrasound detection unit 427 for detecting ultrasound waves induced by the excitation laser is mounted on the platform 427. The ultrasound detection unit 427 comprising a CW laser source (not explicitly shown) focussing a detection laser beam 408 on the running surface of the rail 401 via a mirror 424. The ultrasound detection unit 427 further comprises a CFPI (not explicitly shown) that receives the light from the detection laser beam which is scattered off the running surface of the rail 401, as described in connection with FIG. 1.

It is understood that the laser beams 406 and 408 may be directed to the running surface by a number of different optical arrangements using mirrors, a fibre-optic system, a combination of the above, or the like.

The detection signal generated by the ultrasound detection unit 427 is fed into a signal processing unit 412. In some embodiments, the signal processing unit 412 comprises a data acquisition circuit for acquiring the detection signal from the ultrasound detection unit 427 and a storage device, e.g. a hard disk, for storing the ultrasound scans, preferably in relation with trigger data from the excitation laser and additional data, e.g. data related to the current position of the vehicle, the current speed of the vehicle, etc. The stored data may subsequently be retrieved for off-line analysis of the ultrasound scans, e.g. on a suitably programmed computer. In other embodiments, the signal processing unit further comprises a processor suitably programmed to analyse the acquired waveforms in real time, e.g. as described in connection with FIG. 5 below. The analysis of the scans results in an identification of possible defects, their type and estimated location. The resulting data may be stored as described above. Alternatively or additionally, the results of the analysis process may be presented to an operator in real time. For example, the signal processing unit may be connected to an operator workstation, e.g. on a maintenance railway vehicle, to which the vehicle 420 is attached. In this embodiment, possible defects may be further inspected right away. Furthermore, the detection process may be performed interactively, as will be described below.

The platform 422 is suspended from the frame structure 412 by three actuators 425 allowing the alignment of the platform and, thus, the positions of the focus spots of the excitation laser beam 406 and the detection laser beam 408 with the rail 401. For example, the lateral alignment may be performed by the automatic lateral alignment apparatus for a testing device described in published US patent application US 2001/0032513.

Alternatively or additionally, a lateral alignment of the platform 422 may be achieved by pressing the wheels 426 running on the rail 401 to be tested against the gage side of the rail 401, thereby providing a reliable alignment without the need of complicated control feedback and real-time adjustments of the platform via actuators 425. To this end, the wheels 426 are mounted directly to the frame structure 421. The wheels 428 on the opposite side of the vehicle, i.e. the wheels running on the rail 430 which is not tested, are connected to the frame structure 421 via respective compressed-air cylinders 429, spring members, or the like, for applying a pressure along the axis of rotation of the wheels 429 and in an outward direction, thereby laterally pressing the wheels 429 against the gage side of rail 430 and the wheels 426 against the gage side of the rail 401 to be inspected. Consequently, since the wheels 426 are directly mounted to the frame structure 421 carrying the platform 422, the platform and, thus, the laser beams are aligned with the rail 401. In order to avoid derailing of the vehicle 420, it is preferred that the vehicle 420 is mounted under a regular railway vehicle that provides the forward traction and holds the vehicle 420 in place.

The platform 422 may further be tilted via the actuators 425, e.g. in order to adjust the angle of incident of the excitation beam 406 and the detection beam 408 with respect to the running surface of the rail. This may be particularly advantageous in situations with non-uniform wear of the running surface causing the running surface to deviate from a horizontal plane.

In the following, the detection process for identifying defects from the acquired waveforms will be described with reference to FIGS. 5 and 6.

Figure 5:
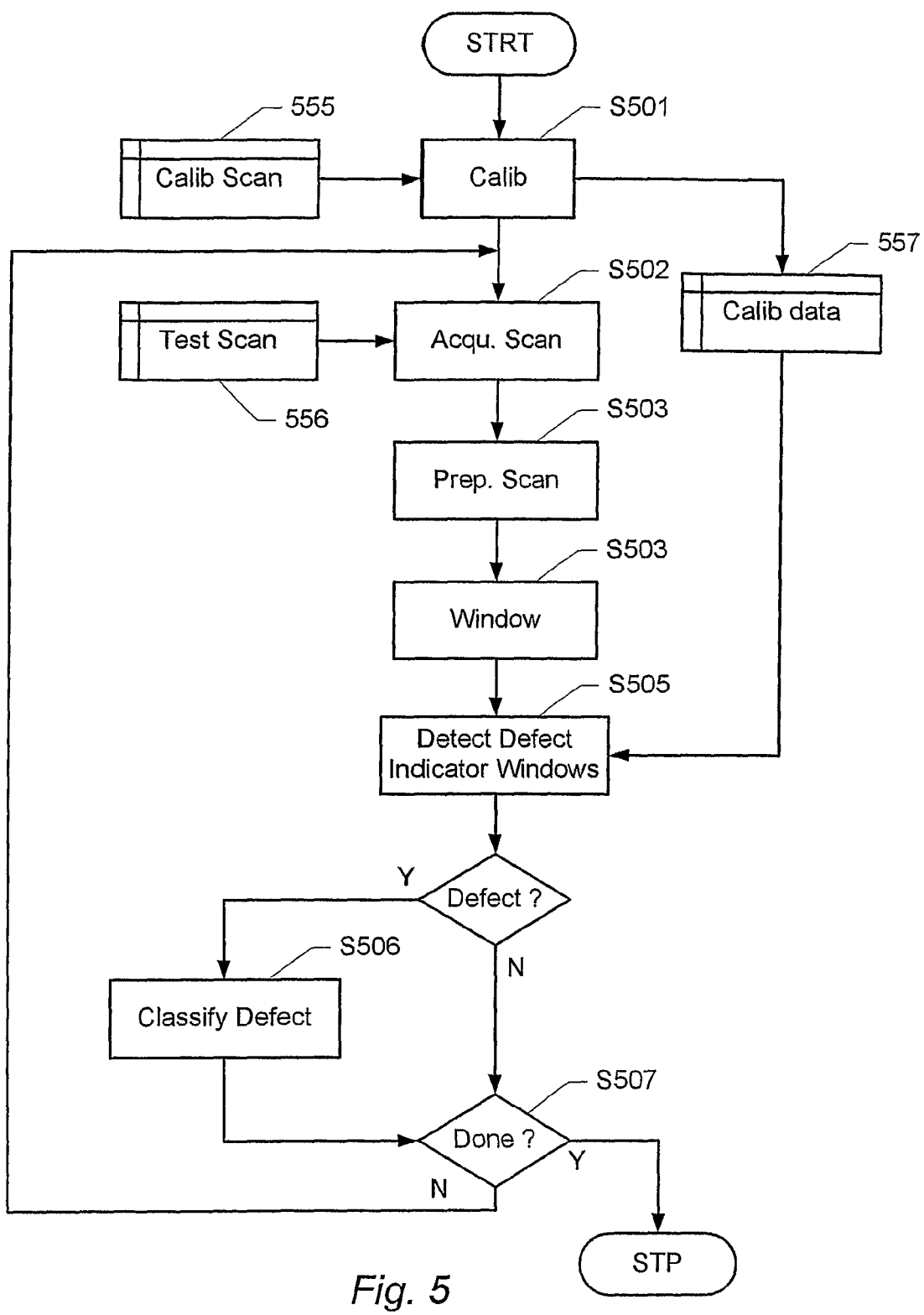
FIG. 5 shows a flow diagram of a detection process for detecting defects in a rail.

FIG. 5 shows a flow diagram of a detection process for detecting defects in a rail. In one embodiment, the process is implemented by a suitable microprocessor, e.g. the signal processing unit 112 of FIG. 1.

In an initial step S501 the process acquires one or more detection signals 555 from a rail section known to be free of defects, or signals which, after an analysis or visual inspection of the resulting waveforms, are determined to correspond to a rail section free of defects. To this end, the process acquires a detection signal from the ultrasonic laser detector, i.e. a waveform of light intensity measured by the CFPI as a function of time, triggered by a firing of the excitation laser. The detection signal is represented as a sequence of signal samples. One or more waveforms from the defect-free rail are processed resulting in a set of calibration parameters 557 as will be apparent and described below.

Once the calibration data is established, the actual inspection of a rail section is initiated in step S502, where the process acquires a waveform 556 of light intensity as a function of time triggered by a firing of the excitation laser. Again, the detection signal is represented as a sequence of signal samples.

FIG. 6 illustrates examples of ultrasound waveforms of rails. The graphs 631, 632, and 633 of FIG. 6 show light intensities measured by the CFPI in arbitrary units as function of time measured in microseconds from the trigger time. Hence, for each of the graphs in FIG. 6, the trigger has occurred at t=0. Graph 631 represents a waveform of a rail section without defects corresponding to a calibration scan, while graphs 632 and 633 represent waveforms of rail sections having defects. Graphs 632 and 633 have been offset along the intensity axis (y-axis), in order to improve readability of the graphs.

The excitation laser induces different types of ultrasonic waves in the rail including a longitudinal (compressional) wave, a Rayleigh wave propagating along the surface of the rail head, and shear waves propagating downwards into the rail head. The different waves propagate at different velocities along the rail, and they interact with defects in different portions of the rail. For example, the longitudinal wave has the highest velocity, approximately 6000 m/s, while the Rayleigh wave travels at approx. 3000 m/s. The Rayleigh wave interacts with defects at or near the surface of the rail head, while the shear waves cause reflections at horizontal bulk defects in the rail head.

The large transient designated 634 corresponds to the Rayleigh wave pulse, i.e. the arrival of the Rayleigh wave pulse at the detection position. The graph 635 corresponds to a rail section having a horizontal defect in the rail head causing a reflection of the shear wave. The echo from this reflection is detected in the waveform as a transient 635. Graph 633 corresponds to a rail section having a surface defect causing an echo of the Rayleigh wave pulse resulting in an echo pulse 636.

Again referring to FIG. 5, in subsequent step S503, the process performs a digital band-pass filtering and a scaling of the signal. For example, the signal may be scaled to its overall standard deviation of the signal values.

The process continues at step S504 where the filtered and scaled waveform is rectified, e.g. by generating the absolute value |A(t)| of the waveform A(t), and windowed, i.e. divided into a sequence of signal segments. The width of the windows is selected to correspond to the typical width of the Rayleigh wave transient 634. In FIG. 6, the windows are illustrated by vertical dotted lines and designated 640-1, 640-2, 640-3, ..., 640-15. In the example of FIG. 6, the width of the windows is approximately 1.2 µs.

In step S505, for each of the windows, the maximum peak height of the waveform in the window (i.e. the maximum value of signal samples) and the standard deviation of signal samples in that window are calculated. The calculated peak height and standard deviation for each window are compared with the peak height and standard deviation of the corresponding window in the calibration scan. Furthermore, the calculated peak height and standard deviation for each window are compared with the peak height and standard deviation of the windows of the same scan adjacent to the current window. If the peak height and the standard deviation exceed both the corresponding values of the calibration scan and the corresponding values of the adjacent windows, the current window is identified as a defect indicator window.

The above comparisons may be illustrated by the example of window 640-10 in graph 633 of FIG. 6, assuming that graph 631 represents the corresponding calibration scan. The peak height and standard deviation of window 640-10 of graph 633 are larger than the corresponding values of window 610-10 of the calibration scan 631, and they are larger than the corresponding values of the adjacent windows 640-9 and 640-11 of scan 633. Hence, the process would classify window 640-10 as a defect indicator window. In comparison, the corresponding test for window 640-9 of graph 633 would yield a negative result. Even though the peak height and standard deviation of window 640-9 are larger than the values of window 640-9 of the calibration scan 631, the peak height and standard deviation of window 640-9 are smaller than the corresponding values of one of its adjacent windows, namely window 640-10 of scan 633.

It is understood that, alternatively or additionally other parameters indicative of the presence of a pulse in a window may be used for the comparison.

It is an advantage of the above method that it utilises a comparison with a calibration scan, thereby avoiding the need of making a priori assumptions about the shape of the waveforms, the expected location of peaks, etc.

Furthermore, it is an advantage of the additional comparison with adjacent windows, that a higher resolution of the pulse detection is achieved.

It is further understood, that instead of the above conditions of step S505 for detecting a defect indicator window alternative conditions may be used. For example, in one embodiment a window may be detected as defect indicator window only if the peak height and standard deviation of that window exceed the corresponding values of the calibration window and of the adjacent windows by a predetermined margin, thereby introducing a trade-off between the number of false positive and the number of false negative detections.

If the comparisons of step S505 have resulted in the identification of one or more defect indicator windows, the process proceeds at step S506 where a defect classification routine is executed; otherwise the process proceeds to step S507, where it is tested whether there are additional scans to be processed. If this is the case the process returns to step S502 where the next scan is acquired and subsequently analysed. If all scans have been processed the process terminates.

The defect classification routine of step S506 receives the data from the one or more identified defect indicator windows. For each of the identified windows, the process calculates wave tracks of longitudinal, shear, and Rayleigh waves from the known velocities of the different wave types and compares the wave tracks with the rail geometry. If the tracking leads to points inside the rail body for bulk ultrasonic wave velocities, or if the tracking leads to points on the running surface for Rayleigh velocities, the process identifies the corresponding defect type and approximate location. An example of the above tracking and defect classification will be described in connection with step 18 of the example process described below. In one embodiment, the process issues an alarm, e.g. via a suitable operator interface. Additionally or alternatively, the detection results may be logged for subsequent further analysis.

After completion of the defect classification step S506, the process proceeds at step S507 described above.

The acquisition of the calibration detection signal of step S501 is performed by performing the filtering, scaling, rectification, and windowing as in steps S503 and S504 above. Subsequently, the process calculates and stores the peak heights and standard deviations for each of the windows resulting in calibration peak heights and calibration standard deviations for use in the comparison of step S505. It is understood that the calibration peak heights and standard deviations may be determined as averages of the corresponding values for a number of calibration scans.

In the following an example of a detection process is described in greater detail. The following example illustrates an interactive process involving operator inputs. Hence, this example is particularly suited for an off-line analysis of previously acquired scans.

EXAMPLE PROCESS

Stage A—Initial Input and Calibration:

Step 1: Input/define wave velocities (in mm/μs), i.e. constants $C_L$ (longitudinal wave velocity), $C_T$ (shear wave velocity), and $C_R$ (Rayleigh wave velocity).

Step 2: Input a source-receiver separation $S_{RS}$ (in mm), i.e. the distance between the excitation position and the detection position, and relevant dimensions of the rail, e.g. the depth $D_{wf}$ of the web fillet and the height of the rail.

It is understood that some or all of the above parameters may be stored by the system, thereby avoiding the need to re-enter the parameters every time the same type of rail is examined and/or the same type of detection apparatus is used.

Step 3: Read a sequence of acquired A-scans.

Step 4: Cut off the leading sections of the A-scans from t=0 to a time $t=S_{RS}/C_L$, i.e. from the trigger event to the arrival of the surface-skimming bulk longitudinal wave having the highest velocity and the shortest track. The leaders do not carry information about defects.

Step 5: Display a first A-scan in the sequence and request and operator input indicative of an accept/rejection of the displayed scan as being representative enough to start the processing. If the operator rejects the A-scan, repeat step 5 for the next A-scan in the sequence. If the operator accepts the A-scan as representative, continue at step 6.

Step 6: Input the lower (LAF) and higher (HF) cut-off frequencies (in MHz) for the A-scan filtering.

Step 7: Perform band-pass filtering, e.g. a Butterworth band-pass filters, to the accepted representative A-scan.

Step 8: Receive an operator input (e.g. by selecting a segment of the displayed graph with a pointing device) indicating a representative segment/window of the A-scan for normalization.

Step 9: Calculate the standard deviation (SDV) of the signal samples in the selected window and normalize the A-scan to the calculated SDV.

Step 10: Display the normalized A-scan and request an operator input indicating an operator approval to continue processing of the rest of the A-scans sequence with the current filter and normalization parameters. If no, return to step 6. If yes, continue at step 11.

Step 11: Receive an operator input (e.g. by selecting a segment of the displayed graph with a pointing device) indicating a part of the A-scan to be used for the subsequent analysis. Preferably, the part is selected to be a segment between the Rayleigh pulse and the arrival of the blast wave. The airborne blast wave is caused by the laser ablation of the solid surface, and its arrival at the detection spot is detected as a variation of the light intensity of the detection laser beam caused by a deflection of the laser beam due to the change of refractive index of the air.

Step 12: Receive an operator input (e.g. by selecting a segment of the displayed graph with a pointing device) indicating a width of the windows used in the subsequent segmentation of the (selected part of the) A-scan. For example, the width may be selected to approximate the width of the Rayleigh wave pulse.

Step 13: Divide the selected part of the A-scan into windows of the selected width, and calculate SDV and peak height (PK), and store the calculated values as calibration parameters.

Stage B—Identification of Defects:

Step 14: Read a new A-scan of a rail section to be tested for defects and process the new A-scan as in steps 7 and 9 and with the filter parameters and normalisation parameters determined during the calibration stage.

Step 15: Display the A-scan and request the operators' permission to continue processing of the current A-scan. If no, return to the step 14 to read a new scan. If yes, continue at step 16.

Step 16: segment the A-scan and calculate the SDV and PK for each window as in step 13 and with the parameters determined during calibration, i.e. the selected width of the windows and for the selected part of the A scan.

Step 17: Compare the calculated SDV and PK in each window with the corresponding stored calibration SDV and PK values and with the values in the left and right adjacent windows. If in one of the windows of the current A-scan both SDV and PK are greater than both the corresponding calibration values and the values of the adjacent windows of the current A-scan, identify the current window as defect indicator window, determine the left bound of the defect indicator window $T_{IWL}$, determine the right bound of the defect indicator window $T_{IWR}$ (both in μs), and go to the step 18. Otherwise, display 'No indication of defects found,' and return to the step 14 to process the next scan. In an alternative embodiment, only one of the above parameters SDV and PK are used as criteria. Using both the peak height and the SDV as detection criteria for defect indicator windows reduces the risk of decision-making errors.

Step 18: Using the determined bounds $T_{IWL}$ and $T_{IWR}$ of the indication window, the input wave velocities $C_L$, $C_T$, and $C_R$, the source-receiver distance $S_{RS}$, the depth $D_{wf}$ to the web fillet, and the height $H_R$ of the rail, determine the type and approximate position of the defect. The analysis may be expressed in pseudocode as follows:

```
IF ( (0.5·T_IWL·C_L)² − (0.5*S_RS)²)>0 AND (0.5·T_IWL·C_L)² − (0.5*S_RS)² ≦ (0.5·H_R)² )
THEN
{
```

$$D_{LH} = \sqrt{(0.5 \cdot T_{IWL} \cdot C_L)^2 - (0.5 \cdot S_{RS})^2}$$

$$D_{LL} = \sqrt{(0.5 \cdot T_{IWR} \cdot C_L)^2 - (0.5 \cdot S_{RS})^2}$$

```
    IF(D_LL < D_wf)THEN
        Display 'Suspect of defect type UIC 212 at D_LH ... D_LL mm depth'
    ELSE
        Display 'Suspect of defect type UIC 232 at D_LH ... D_LL mm depth'
}
ELSE IF ( (0.5·T_IWL·C_T)² − (0.5*S_RS)²)>0 AND
```

-continued

```
        (0.5·T_IWL·C_T)² - (0.5*S_RS)²) ≦ (0.5·D_wf)² ) THEN
{
                D_TH = √((0.5·T_IWL·C_T)² - (0.5·S_RS)²)

D_TL = √((0.5·T_IWR·C_T)² - (0.5·S_RS)²)

Display 'Suspect of defect type UIC 212 at D_TH . . . D_TL mm depth'
}
ELSE
{
        Display 'Suspect surface-breaking defect'
}
ENDIF
```

In the above pseudocode example, the first condition $((0.5 \cdot T_{IWL} \cdot C_L)^2 - (0.5 * S_{RS})^2) > 0$ AND $(0.5 \cdot T_{IWL} \cdot C_L)^2 - (0.5 * S_{RS})^2) \leq (0.5 \cdot H_R)^2)$ tests whether the detected burst in the defect indicator window starting at $T_{IWL}$ results from an echo of a longitudinal wave. The expression $((0.5 \cdot T_{IWL} \cdot C_L)^2 - (0.5 * S_{RS})^2$ corresponds to the squared depth from the surface to the reflector of the longitudinal wave, i.e. the squared depth to the defect. If the depth is greater than zero and smaller than a maximum depth related to the height of the rail squared than the detected event is classified as a reflection of the longitudinal wave at a defect within the rail reflection is caused by a longitudinal wave. If this condition is fulfilled, the defect is classified as bulk defect of the head. The approximate depth of the location is estimated from the bounds of the defect indicator window and the velocity of the longitudinal wave. The estimated depth is expressed as an interval having a lower bound $D_{LL}$ and an upper bound $D_{LH}$ determined from the bounds of the defect indicator window. Depending of the estimated depth compared to the dimensions of the head, the defect type is further specified as UIC 212 or UIC 232, respectively, depending on the estimated depth compared to the depth $D_{wf}$ of the web fillet. For an UIC 60 rail, the depth $D_{wf}$ is approximately 65 mm.

If the first condition is not fulfilled, a second condition is tested, i.e. $((0.5 \cdot T_{IWL} \cdot C_T)^2 - (0.5 * S_{RS})^2) > 0$ AND $(0.5 \cdot T_{IWL} \cdot C_T)^2 - (0.5 * S_{RS})^2) \leq (0.5 \cdot D_{wf})^2)$. This condition tests whether the detected pulse originates from an echo of a shear wave where the boundaries of the depth are between zero and a maximum depth related to the vertical dimension of the rail head. If the condition is fulfilled, the defect is classified as a horizontal cracking of the head, and the estimated depth is determined as described above.

Finally, if the estimated depth is less or equal zero, the registered event is classified as a reflection of a surface wave transient at a surface-breaking defect.

Step 19: Request an operator input confirming/overriding the determined defect type.

Step 20: Return to the step 14 to process the next A-scan.

It is understood that the above process, and in particular the identification of defects once a calibration is performed, may easily be adapted to run automatically, thereby allowing a real-time analysis without operator input. For example, the operator input of step 15 may be omitted, i.e. the scans may continuously be analysed without additional operator interference. Likewise, step 19 is optional in an automatic detection process.

It is further understood that the above process may be used in connection with both the configuration of FIGS. 2a-b and of FIGS. 3a-c.

Figure 7A:
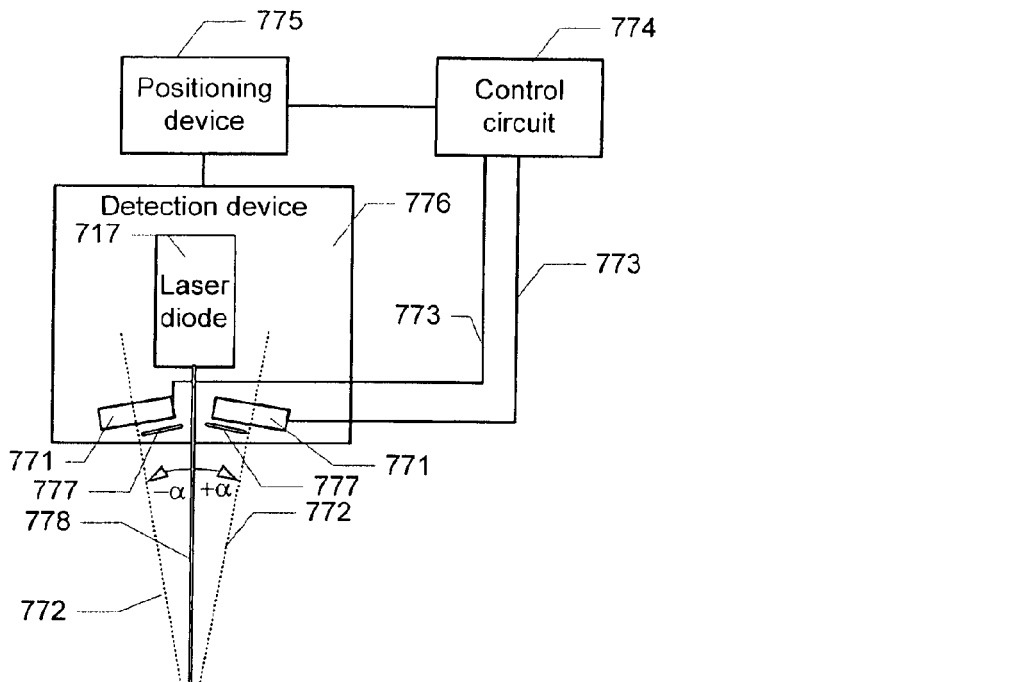
FIGS. 7a-b illustrate an arrangement for adjusting the incident angle of the detection laser beam.
Figure 7B:
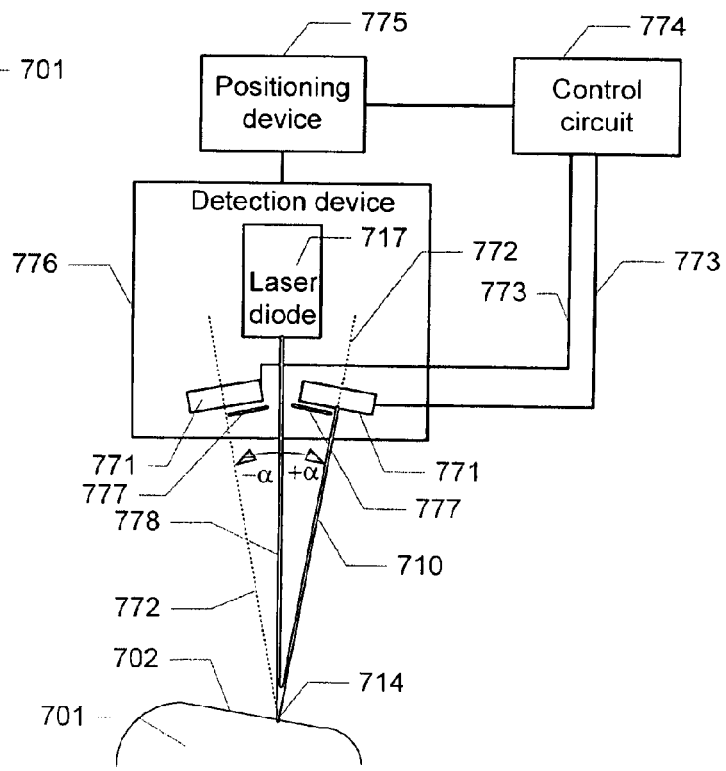

FIGS. 7a-b illustrate an arrangement for adjusting the incident angle of the detection laser beam. FIGS. 7a-b show the detection device 776 to be angularly aligned with the running surface 702 of the rail 701. For example, the detection device 776 may be the detection device 176 of FIG. 1 comprising the detection laser and the interferometer (not explicitly shown in FIGS. 7a-b).

The detection device comprises a laser diode 717 and two photodiodes 771. The laser diode 717 directs a probe beam 778 to a position 714 on the running surface 702 of the rail 701. The photodiodes are adapted to receive reflected laser light from the position 714 at respective predetermined angles $\pm\alpha$ with respect to the direction of the probe beam and in a lateral plane with respect to the rail 701, as illustrated by dotted lines 772. For example, the arrangement may comprise apertures or spatial filters 777 allowing only light reflected from the position 714 at at least a predetermined angle to reach the respective photodiodes.

While the probe beam 778 in the situation depicted in FIG. 7a hits the running surface substantially perpendicular with respect to the surface 702, the running surface 702 in FIG. 7b is inclined causing the probe beam 708 to have an incident angle different from 90°. This causes the reflected probe beam 710 to be reflected at an angle different from 0° with respect to the probe beam 778. Since the inclination of the running surface also affects the detection laser beam of the laser ultrasonic detection device described above, it may cause a misalignment of the reflected detection laser beam with the interferometer. For example, the running surface may be inclined from the plane defined by the rails of the railway track, i.e. typically from a substantially horizontal plane, due to non-uniform wear of the rails, in particular in curves.

Figure 6B:
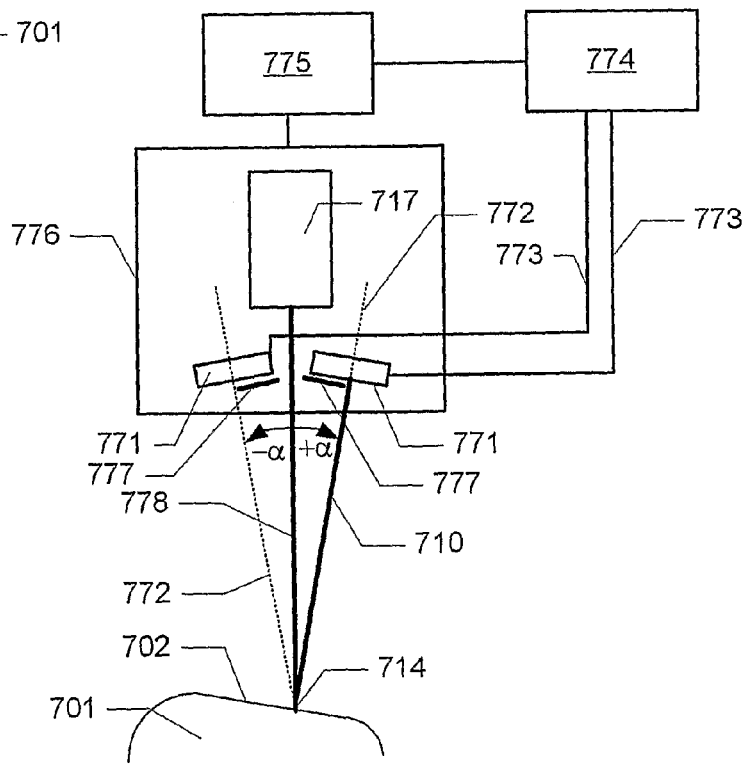

When the inclination of the running surface is larger than $\pm\alpha/2$, the reflected beam 711 hits one of the photodiodes as illustrated in FIG. 6b. The corresponding signal generated by the photodiode 771 is fed into a control circuit 774 for controlling a positioning device 775 adapted to adjust the inclination of the detection device 776. For example, if the right photodiode sends a signal to the control circuit 774, the control circuit 774 controls the positioning device 775 to tilt the detection device 776 by an angle $2\alpha$ to the left, thereby readjusting the probe beam to perpendicularly hit the running surface as in FIG. 7a. For example, the positioning device may comprise a number of linear and/or rotational actuators for positioning the detection device 776 with respect to a support structure.

Hence, the above arrangement causes the lateral angular misalignment of the probe beam and, thus, of the detection laser beam to be no larger than ±α. The actually value of α depends on the opening aperture of the interferometer and on the distance between the interferometer from the rail. In a preferred embodiment, the lateral angular tolerance is α<5°, preferably α<2°, more preferably α<1°.

It is understood that, in some embodiments, the detection device 776 further comprises the excitation laser, thereby providing a simultaneous angular alignment of both the detection laser beam and the excitation laser beam of a laser-ultrasonic detection device as described above. For example, the detection device 776 may be embodied as a platform carrying the various components of the detection device, e.g. the platform 422 of FIG. 4.

It is further understood that, instead of the photodiodes, other detectors sensitive to the laser light from the probe laser 717 may be used. For example, position sensitive detectors, e.g. including an array of photodiodes, may be used instead of the photodiodes 771, thereby allowing the measurement of the actual incident angle and, thus, the generation of a more accurate feedback signal.

It is further understood that, instead of a separate probe beam 778 generated by a probe laser diode 717, the angular adjustment may be performed based on a directly detected angular misalignment of the detection laser beam.

Although preferred embodiments of the present invention have been described and shown, the invention is not restricted to them, but may also be embodied in other ways within the scope of the subject matter defined in the following claims.

The invention can be implemented by means of hardware comprising several distinct elements, by means of a suitably programmed microprocessor, and/or by a combination thereof.

In the device claims enumerating several means, several of these means can be embodied by one and the same item of hardware, e.g. a suitably programmed microprocessor, one or more digital signal processor, one or more ASIC circuit, or a combination of the above. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The invention claimed is:

1. A method of detecting defects in a railway track rail, the rail having a longitudinal centre plane and a surface, the surface including a running surface, the method comprising
   directing an excitation laser beam to an excitation position on the surface of the rail to induce an ultrasonic wave in the rail; and
   directing a detection laser beam to a detection position on the surface of the rail to detect at least one predetermined property of the induced ultrasonic wave;
   characterised in that the excitation position and the detection position are located on the running surface and displaced from the longitudinal centre plane of the rail.

2. A method according to claim 1, wherein the excitation position is located on a first side of the longitudinal centre plane and wherein the detection position is located on a second side of the longitudinal centre plane opposite the first side.

3. A method according to claim 2, wherein the excitation position is displaced from the longitudinal centre plane by an excitation distance; and wherein the detection position is displaced from the longitudinal centre plane by a detection distance, the detection distance being substantially equal to the excitation distance.

4. A method according to claim 2, wherein the rail comprises a rail web portion supporting a rail head, the rail web portion having a web waist defining a minimum cross sectional width of a rail web; and wherein the detection position is displaced from the excitation position in a cross direction of the rail by a transverse spot displacement corresponding to half the minimum cross sectional width of the rail web.

5. A method according to claim 1, wherein the detection position is displaced in a longitudinal direction of the rail from the excitation position by a longitudinal spot displacement.

6. A method according to claim 5, wherein the rail comprises a rail head having a predetermined width; and wherein the longitudinal spot displacement corresponds to a half the width of the rail head.

7. A method according to claim 2, further comprising detecting from the at least one predetermined property of the induced ultrasonic wave the presence or absence of a rail defect of a predetermined defect type; wherein the defect type is selected from the group of defect types consisting of a horizontal cracking at a web-head fillet radius, a horizontal crack of a rail head, a progressive crack of the head, and a complete rail break.

8. A method according to claim 1, wherein the rail comprises a gage side proximate to a centre of a railway track; and wherein the excitation position and the detection position are located on the gage side of a longitudinal axis.

9. A method according to claim 8, wherein the rail comprises a rail web portion supporting a rail head, a rail web portion having a web waist defining a minimum cross sectional width of the rail web; and wherein the detection position is displaced from the longitudinal centre plane by a detection distance corresponding to half the minimum cross sectional width of the rail.

10. A method according to claim 8, further comprising detecting from the at least one predetermined property of the induced ultrasonic wave the presence or absence of a rail defect of a predetermined defect type; wherein the defect type is selected from the group of defect types consisting of a longitudinal vertical crack of a rail head and a long groove of the running surface.

11. A method according to claim 1, wherein an excitation spot is an elongated spot.

12. A method according to claim 11, wherein the elongated spot defines a longitudinal excitation spot direction, and wherein the longitudinal excitation spot direction is transverse with respect to the direction of the displacement of the detection position from the excitation position.

13. A method according to claim 1, wherein the detection position and the excitation position are moved along a longitudinal direction of the rail at a predetermined speed.

14. A method according to claim 1, wherein the detection laser beam is a continuous-wave laser connected to an optical interferometer.

15. A method according to claim 1, further comprising
   receiving a scattered laser beam produced from the detection laser beam scattered at the surface of the rail and modulated corresponding to the ultrasonic wave with an optical interferometer;
   generating an output signal of the optical interferometer representative of the ultrasonic wave.

16. A method according to claim 1, further comprising
   obtaining a first ultrasonic waveform corresponding to an ultrasonic wave induced into a first rail segment;

dividing the first ultrasonic waveform into a set of waveform segments;

determining at least a first waveform parameter indicative of at least one predetermined property of a first waveform segment;

determining the first waveform segment as being indicative of the presence or absence of a rail defect in the first rail segment by comparing the determined first waveform parameter with at least one reference waveform parameter.

17. An apparatus for detecting defects in a railway track rail, the rail having a longitudinal centre plane and a surface, the surface including a running surface, the apparatus comprising an excitation laser arrangement adapted to direct an excitation laser beam to an excitation position on the surface of the rail to induce an ultrasonic wave in the rail;

and a detection laser arrangement adapted to direct a detection laser beam to a detection position on the surface of the rail to detect a predetermined property of the induced ultrasonic wave;

characterised in that the excitation laser arrangement and the detection laser arrangement are arranged to direct the excitation laser beam and the detection laser beam to respective excitation and detection positions located on the running surface and displaced from the longitudinal centre plane of the rail.

18. An apparatus according to claim 17, the apparatus further comprising a rail vehicle adapted to be moved along the rail; wherein the excitation laser arrangement and the detection laser arrangement are mounted to the rail vehicle.

19. An apparatus according to claim 17, further comprising control means for adjusting an incident angle of the detection laser beam on the running surface of the rail.

20. A method of detecting defects in a railway track rail, the method comprising obtaining a first ultrasonic waveform corresponding to an ultrasonic wave induced into a first rail segment;

dividing the first ultrasonic waveform into a set of waveform segments;

determining at least a first waveform parameter indicative of at least one predetermined property of a first waveform segment;

determining the first waveform segment as being indicative of the presence or absence of a rail defect in the first rail segment by comparing the determined first waveform parameter with at least one reference waveform parameter.

21. A method according to claim 20, wherein the at least one predetermined property includes at least one of a standard deviation and a peak height.

22. A method according to claim 20, wherein the at least one reference waveform parameter includes at least one of a waveform parameter of a corresponding waveform segment of a calibration waveform and a waveform parameter of a second waveform segment of the first ultrasonic waveform, the second waveform segment being adjacent to the first waveform segment.

23. A method according to claim 20, further comprising determining a defect type and a defect location from a location within the obtained waveform of at least one waveform segment determined as being indicative of the presence of a rail defect in the first rail segment.

24. A data processing system comprising means for obtaining a first ultrasonic waveform corresponding to an ultrasonic wave induced into a first rail segment;

and processing means adapted to divide the first ultrasonic waveform into a set of waveform segments;

determine at least a first waveform parameter indicative of at least one predetermined property of a first waveform segment;

determine the first waveform segment as being indicative of the presence or absence of a rail defect in the first rail segment by comparing the determined first waveform parameter with at least one reference waveform parameter.

25. A computer-readable medium having stored thereon a computer program comprising program code means performing, when said program is run on a computer, the steps of:

obtaining a first ultrasonic waveform corresponding to an ultrasonic wave induced into a first rail segment;

dividing the first ultrasonic waveform into a set of waveform segments;

determining at least a first waveform parameter indicative of at least one predetermined property of a first waveform segment; and determining the first waveform segment as being indicative of the presence or absence of a rail defect in the first rail segment by comparing the determined first waveform parameter with at least one reference waveform parameter.

26. A computer program product comprising program code means stored on a computer readable medium for performing the steps of:

obtaining a first ultrasonic waveform corresponding to an ultrasonic wave induced into a first rail segment;

dividing the first ultrasonic waveform into a set of waveform segments;

determining at least a first waveform parameter indicative of at least one predetermined property of a first waveform segment; and determining the first waveform segment as being indicative of the presence or absence of a rail defect in the first rail segment by comparing the determined first waveform parameter with at least one reference waveform parameter.

* * * * *